United States Patent [19]
Kim et al.

[11] Patent Number: 5,389,627
[45] Date of Patent: Feb. 14, 1995

[54] CEPHEM COMPOUNDS

[75] Inventors: Choong S. Kim; Yang S. Ahn, both of Seoul; Kang Y. Jung, Kyonggi-do; Nam H. Lee, Seoul; Rok L. Yun, Kyonggi-do; Seong Y. Park; Yeo H. Yoon, both of Seoul; Keon H. Lee, Kyonggi-do; Chun S. Lyu; Kwang H. Lee, both of Seoul, all of Rep. of Korea

[73] Assignee: Cheil Foods & Chemicals, Seoul, Rep. of Korea

[21] Appl. No.: 145,228

[22] Filed: Nov. 3, 1993

[30] Foreign Application Priority Data

Jun. 5, 1993 [KR] Rep. of Korea ................ 1993-10188

[51] Int. Cl.$^6$ ................ C07D 501/38; A61K 31/545
[52] U.S. Cl. ..................................... 514/202; 514/206; 540/222; 540/225
[58] Field of Search ................ 540/225, 222, 221; 514/206, 202

[56] References Cited

U.S. PATENT DOCUMENTS

| | | |
|---|---|---|
| 4,098,888 | 7/1978 | Ochiai et al. . |
| 4,152,432 | 5/1979 | Heymes et al. . |
| 4,258,041 | 3/1981 | O'Callaghan et al. . |
| 4,266,049 | 5/1981 | Bonjouklian . |
| 4,748,172 | 5/1988 | Katner . |
| 5,281,589 | 1/1994 | Kim et al. ............... 514/206 |

FOREIGN PATENT DOCUMENTS 0164944 12/1985 European Pat. Off. .

*Primary Examiner*—Nicholas Rizzo
*Attorney, Agent, or Firm*—Burns, Doane, Swecker & Mathis

[57] ABSTRACT

The present invention relates to novel cephem compounds having the formula:

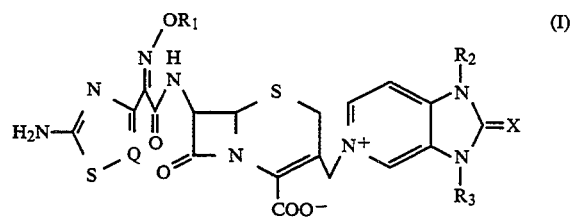

wherein, Q is a carbon or nitrogen atom; X is an oxygen atom, or a nitroalkyl or cyanoimine group, with the proviso that X cannot be an oxygen atom when Q is a carbon atom; $R_1$ is a hydrogen atom, or a lower alkyl group, or a lower alkyl group which may be substituted by fluoro, or by a carboxylic group or an inorganic cation salt thereof; and $R_2$ and $R_3$ independently are a hydrogen atom or a lower alkyl group; or pharmaceutically acceptable salts thereof.

The compounds of the present invention have potent antibacterial activities against gram-negative bacteria, especially Pseudomonas, and a longer half-life than conventional cephem compounds.

8 Claims, No Drawings

CEPHEM COMPOUNDS

BACKGROUND OF THE INVENTION

1. Field of the Invention

The present invention relates to novel cephem compounds and pharmaceutically acceptable salts thereof having potent antibacterial activities against gram-negative bacteria and an extended duration of action.

2. Description of the Prior Art

Since the first synthesis of cephem compounds in which the cephem nucleus has a carboxylic group at 4-position and a substituted amino group at 7-position, an extensive investigation has been made to develop a novel structure of cephem derivatives having more potent antibacterial activities and a broad antibacterial spectrum.

As prior art references which disclose such derivatives, U.S. Pat. No. 4,152,432 to Heymes et al.; U.S. Pat. No. 4,098,888 to Ochiai et al.; U.S. Pat. No. 4,258,041 to O'Callaghan; U.S. Pat. No. 4,748,172 to Katner; European Patent No. 0,318,552 to Katner; European Patent No. 0,164,944 to Bradbury; and European Patent No. 0,300,664 to Jung may be mentioned.

In most recent years, we have proposed, in our U.S. Ser. No. 07/896,667, now U.S. Pat. No. 5,281,589, a class of novel compounds having the formula:

[chemical structure]

SUMMARY OF THE INVENTION

We have now found an another class of novel compounds which are neither described nor claimed in U.S. Ser. No. 07/896,667, now U.S. Pat. No. 5,281,589. These noval compounds have been proven by the present invention to have potent antibacterial activities against gram-negative bacteria, especially Pseudomonas, and a significantly long duration of action.

DETAILED DESCRIPTION OF THE INVENTION

Thus, in an aspect, the present invention provides novel cephem compounds having the formula:

[chemical structure] (I)

wherein, Q is a carbon or nitrogen atom; X is an oxygen atom, or a nitroalkyl or cyanoimine group, with the proviso that X cannot be an oxygen atom when Q is a carbon atom; $R_1$ is a hydrogen atom, a lower alkyl group, or a lower alkyl group which may be substituted by fluoro, or by a carboxylic group or an inorganic cation salt thereof; and $R_2$ and $R_3$ independently are a hydrogen atom or a lower alkyl group; or pharmaceutically acceptable salts thereof.

As used herein, the term "lower alkyl" refers to alkyl groups having 1 to 5 carbon atoms, such as methyl, ethyl, propyl, isopropyl, tert-butyl, butyl, or pentyl, unless otherwise indicated.

Pharmaceutically acceptable salts of the compounds of the formula (I) include an inorganic cation salt, for example, an alkali metal salt (e.g., sodium salt, potassium salt, etc.), an alkaline earth metal salt (e.g., calcium salt, magnesium salt, etc.); an inorganic acid salt (e.g., hydrochloride, hydrobromide, hydroiodide, sulfate, carbonate, bicarbonate, etc.); an organic acid salt (e.g., maleate, lactate, tartarated, etc.); a sulfonate (e.g., benzenesulfonate, methanesulfonate, paratoluenesulfonate, etc.); a salt with an amino acid such as arginine, lysine, glycine, etc.; and an amine salt (e.g., ammonium salt, trimethylamine salt, triethylamine salt, pyridine salt, procaine salt, picoline salt, etc.), and the like.

Particularly preferred specific compounds according to the invention are as set forth below:

7-β-[(Z)-2-(2-aminothiazol-4-yl)-2-methoxyiminoacetamido]-3-[2-(1H,3H)-nitromethylen-yl-imidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[2-(1H,3H)-nitromethylen-yl-imidazo[4,5-c]pyridiniummethyl]-3-cephem-4-carboxylate;

7-β-[(Z)-2-(2-aminothiazol-4-yl)-2-methoxyiminoacetamido]-3-[2-(1H,3H)-cyanoimineimidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[2-(1H,3H)-cyanoimineimidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[2-(1H,3H)-oxoimidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[1-methyl-2(3H)-oxoimidazo[4,5-c]pyridiniummethyl]-3-cephem-4-carboxylate;

7-β-[(Z)-2-(5-amino-1,2,4-thiadiazol-3-yl)-2-hydroxyiminoacetamido]-3-[2-(1H,3H)-oxo-imidazo[4,5-c]pyridiniummethyl]-3-cephem-4-carboxylate;

7-β-[(Z)-2-(5-amino-1,2,4-thiadiazol-3-yl)-2-carboxymethoxyiminoacetamido]-3-[2-(1H,3H)-oxo-imidazo[4,5-c]pyridiniummethyl]-3-cephem-4-carboxylate; and 7-β-[(Z)-2-(5-amino-1,2,4-thiadiazol-3-yl)-2-fluoromethoxyiminoacetamido]-3-[2-(1H,3H)-oxo-imidazo[4,5-c]pyfidiniummethyl]-3-cephem-4-carboxylate.

The most preferred compounds of the invention are those in which Q is a nitrogen atom; X is an oxygen atom; $R_1$ is a hydrogen atom, a methyl, fluoromethyl or carboxymethyl group; at least one of $R_2$ and $R_3$ is a hydrogen atom.

The compounds according to the present invention have a long duration of action (half-life) and exhibit potent antibacterial activities against gram-negative bacteria such as Pseudomonas.

The compounds of the formula (I) and pharmaceutically acceptable salts thereof can be prepared by reacting a compound having the formula (II):

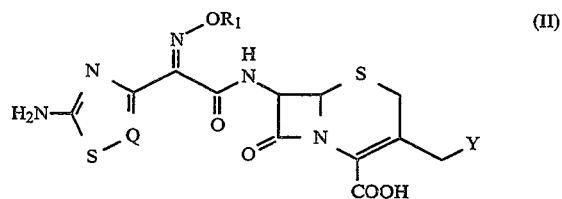

(II)

wherein, Q and $R_1$ have the same meanings as defined above; and Y is a halogen atom or an acetoxy group; with a compound having the formula (III):

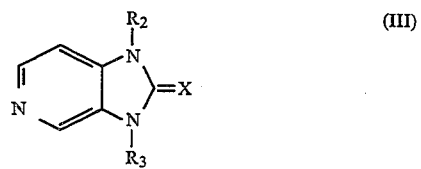

(III)

wherein, X, $R_2$ and $R_3$ have the same meanings as defined above.

Preferably, the halogen atom may include chlorine, bromine or iodine, more preferably iodine.

According to the invention, a compound of the formula (II) is first silylated with a silylating agent in an aprotic organic solvent to protect the carboxy group at 4-position and the amino group at 7-position, of the cephem nucleus.

Such a silylating agent may include N,O-bis(trimethylsilyl)acetamide, N-methyl-N(trimethylsilyl)acetamide, N,O-bis(trimethylsilyl)trifluoroacetamide, N-methyl-N-(trimethylsilyl)trifluoroacetamide, and hexamethyldisilazane. As an appropriate aprotic organic solvent, there may be mentioned nitriles such as acetonitrile and propionitrile; alkyl halides such as chloroform, carbon tetrachloride and dichloromethane; ethers such as tetrahydrofuran and dioxane; amides such as N,N-dimethylformamide; esters such as ethylacetate and methylacetate; ketones such as acetone, methylethylketone and methylisobutylketone; sulfoxides such as dimethylsulfoxide; and aromatic hydrocarbon solvents such as benzene and toluene.

The silylated compound of the formula (II) is then reacted with trimethylsilyliodide (TMSI) at ambient temperature to give a compound of the formula (II) in which Y is iodine. This reaction is disclosed, for example, in U.S. Pat. No. 4,266,049 to Bonjouldian and U.S. Pat. No. 4,748,172 to Katner.

A compound of the formula (III), 2-oxoimidazo pyridine compound, may also be prepared by known methods [See: J. Chem. Soc. (B), 285(1966); J. Org. Chem. 33(6), 2543(1968); J. Org. Chem., 43(3), 393(1978); J. Heterocyclic Chem., 13, 601(1976); J. Heterocyclic Chem., 22, 1061(1985); Syn, Comn., 12(3), 213(1982); Bull. Chem. Soc. Jpn., 60, 1973(1987)], and is silylated with the same silylating agent as mentioned above in an anhydrous aprotic organic solvent.

The silylated 3-iodomethyl cephera compound of the formula (II) is then reacted with a compound of the formula (III) in an anhydrous aprotic solvent to give a silylated compound of the formula (I). Hydrolysis of the silyl group provides a compound of the formula (I) according to the present invention. The resulting compound of the formula (I) is isolated from the reaction mixture and purified by known methods such as extraction using organic solvents, crystallization, column chromatography, and so forth.

The compounds of the present invention may be formulated for administration in the form of an injection (e.g., intravenous, intraperitoneal, intramuscular, or subcutaneous injection) in accordance with conventional methods known in the art. Alternatively, the compounds may be formulated into various kinds of dosage forms, for example, capsules, tablets, pills, solutions, suspensions, emulsions, suppositories, pastes, ointments, gels, creams, lotions, powders, and sprays.

Tablets, capsules, pills and granules can contain the active compound or compounds in combination with the customary excipients, such as fillers and extenders, for example, starches, lactose, sucrose, glucose, mannitol and silica; binders, for example, carboxymethylcellulose, alginates, gelatine and polyvinyl pyrrolidone; humectants, for example, glycerine; disintegrating agents, for example, agar-agar, calcium carbonate and sodium carbonate; absorption accelerators, for example, quaternary ammonium compounds; wetting agents, for example, cetyl alcohol or glycerine monostearate; adsorbents, for example, kaolin and bentonitc; and lubricants, for example, talc, calcium stearate, and magnesium stearate.

Suppositories can contain, in addition to the active compound or compounds, customary aqueous or non-aqueous excipients, for example, polyethylene glycols, fats, for example, cacao fat, and higher esters (for example, a $C_{14}$ alcohol with a $C_{16}$ fatty acid), or mixtures of these substances.

Ointments, pastes, creams and gels can contain customary excipients, in addition to the active compound or compounds, for example, animal and vegetable fats, waxes, paraffins, starch, tragacanth, cellulose derivatives, polyethylene glycols, silicones, bentonites, silica, talc, and zinc oxide, or mixtures of these substances.

Powders and sprays can also contain customary excipients in addition to the active compound or compounds, for example, lactose, talc, silica, aluminum hydroxide, calcium silicate, and polyamide powders, or mixtures of these substances. Sprays can additionally contain customary propellants, for example, chlorofluorohydrocarbons.

Solutions and emulsions can contain customary excipients, in addition to the active compound or compounds, such as solvents, solubilizing agents, and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, corn germ oil, olive oil, caster oil and sesame oil, glycerine, glycerineformal, tetrahydrofuryl alcohol, polyethylene glycols, and fatty acid esters of sorbitan, or mixtures of these substances.

For parenteral administration, the solutions and emulsions can also be in sterile form, which is isotonic with blood.

Suspensions can contain customary excipients, in addition to the active compound or compounds, such as liquid diluents, for example, water, ethyl alcohol or propylene glycol, suspending agents, for example, ethoxylated isostearyl alcohols, polyoxyethylene sorbitol esters and sorbitan esters, microcrystalline cellulose, aluminum meta-hydroxide, bentonite, agar-agar, and tragacanth, or mixtures of these substances.

PREFERRED EMBODIMENTS OF THE INVENTION

The present invention will be described in greater detail by way of the following examples. The examples are presented for illustration purposes only and should not be construed as limiting the invention which is properly delineated in the claims.

PREPARATION 1

2-(1H,3H)-Nitromethylen-yl-imidazo[4,5-c]pyridine

1 G of 1,1-bis(methylthio)-2-nitroethylene and 0.6 g of 3,4-diaminopyridine were placed into a 50 ml reaction vessel. To the mixture was added 20 ml of ethyl alcohol. The resulting dispersion was heated to an elevated temperature and stirred under reflux for 10 hrs, while trapping the methanethiol discharged into an aqueous 20% NaCl solution. Thereafter, the solvent was distilled off under reduced pressure, and the residue was purified by column chromatography on silica gel eluting with dichloroethane:methyl alcohol (2:1) to give 500 mg of the title compound.

IR (KBr, cm$^{-1}$): 3416; 1517; 1319. NMR (DMSO-d$_6$): 7.5(1H, d); 8.2(1H, d); 8.7(1H, s); 7.4(1H, s).

PREPARATION 2

2-(1H,3H)-Cyanoimine-imidazo[4,5-c]pyridine

2 G of dimethyl N-cyanodithioiminocarbonate and 1.34 g of 3,4-diaminopyridine were placed into a 100 ml reaction vessel. To the mixture was added 30 ml of acetonitrile. The resulting dispersion was heated to an elevated temperature and stirred under reflux for overnight, while trapping the methanthiol discharged into an aqueous 20% NaCl solution. After completion of the reaction, the precipitated solids were filtered out and dissolved in dichloroethane:methyl alcohol (2:1), and then separated by column chromatography on silica gel to give 1 g of the title compound.

IR (KBr, cm$^{-1}$): 2180; 1652; 1604; 1488. NMR (DMSO-d$_6$): 7.2(1H, d); 8.2(2H, d); 8.3(1H, s).

PREPARATION 3

2-(1H,3H)-Oxo-imidazo[4,5-c]pyridine

3 G of 3,4odiaminopyridine and 1.65 g of urea were added to 30 ml of dimethylformamide. The mixture was stirred under reflux for 6 hrs, allowed to cool to room temperature, and stirred further for 12 hrs to precipitate solids. The resulting solids were filtered out, and dissolved in methyl alcohol. The resulting solution was treated with active carbon, and concentrated under reduced pressure to give 3.1 g of the title compound as a white solid.

IR (KBr, cm$^{-1}$): 3125; 1717; 1630. NMR (DMSO-d$_6$): 8.14(1H, s); 8.10(1H, d); 6.97(1H, d).

PREPARATION 4

1-Methyl-2(3H)-oxo-imidazo[4,5,c]pyridine 4.3 G of 4-methylamino-3-aminopyridine and 2.1 g of urea were added to 43 ml of dimethylformamide. The resulting mixture was stirred under reflux for 4 hrs, and then allowed to cool to room temperature. The resulting solids were filtered out, and dissolved in methyl alcohol under reflux. The solution was then cooled slowly to precipitate solids. The solution containing the precipitated solids were stirred further for 1 hr and filtered out to give 3.9 g of the title compound as a white solid.

IR (KBr, cm$^{-1}$): 2739; 1715; 1624. NMR (DMSO-D$_2$O): 8.18(1H, s); 8.13(1H, d); 7.1(1H, d); 3.27(3H, s).

EXAMPLE 1

7-$\beta$-[(Z)-2-(2-Aminothiazol-4-yl)-2-methoxyiminoacetamido]-3-[2-(1H,3H)-nitromethylenr-yl-imidazo[4,5-c]pyridiniummethyl-3-cephem-4-carboxylate 500 Mg of 7-$\beta$-[(Z)-2-(2-aminothiazol-4-yl)-2-methoxyiminoacetamido]-3-acetoxymethyl-3-cephem-4-carboxylic acid was suspended in 10 ml of dry dichloromethane. The resulting suspension was added to 0.7 ml of N-methyl-N-(trimethylsilyl)trifluoroacetamide at room temperature. The reaction mixture was stirred for 1 hr to effect silylation. To the silylated solution was added 0.38 ml of iodotrimethylsilane at 0° C. The reaction mixture was stirred for 30 mins at room temperature. Thereafter, the mixture was concentrated, and then the concentrate was dissolved in a mixture of 10 ml of acetonitrile and 1.0 ml of tetrahydrofuran to produce a solution. Separately, 200 mg of 2-(1H,3H)-nitromethylen-yl-imidazo[4,5-c]pyridine was dissolved in a mixture of 10 ml of acetonitrile and 0.79 ml of N,O-bis(trimethylsilyl)acetamide. The resulting solution was subjected to silylation for 1.5 hrs to give a silylated pyridine derivative. The derivative was added to the solution previously obtained, and the mixture was allowed to react at room temperature for 3 hrs. Then, to the reaction mixture was added a mixed solvent of 0.5 ml of methyl alcohol and 5 ml of acetonitrile to effect deprotection. The reaction mixture was stirred at 0 ° C for 30 mins. The resulting solids were filtered out, dissolved in 10 ml of water while adjusting the pH to 6.5 with sodium bicarbonate, and then concentrated. The residue was purified by chromatography on silica gel with acetonitrile:water (4:1) to give 181 mg of the title compound.

IR (KBr, cm$^{-1}$): 3420; 1760; 1670; 1520; 1320. NMR (DMSO-d$_6$): 3.14(1H, d); 3.52(1H, d); 3.76(3H, s); 5.17(1H, d); 530(1H, d), 5.71(1H, d), 5.79(1H, d); 6.69(1H, s); 7.11(2H, br), 8.17(1H, d); 8.45(1H, d); 9.01 (1H, s), 9.53(1H,d).

EXAMPLE 2

7-β-[(Z)-2-(5-Amino-1,2,4-thiadiazol-3-yl)-2-methoxyiminoacetamido]-3-[2-(1H,3H)-nitromethylen-yl-imidazo[4,5-c]-pyridiniummethyl]-3-cephem-4-carboxylate 500 Mg of 7-β-[(Z)-2-(5-amino-1,2,4-thiadiazol-3-yl)-2-methoxyiminoacetamido]-3-acetoxymethyl-3-cephem-4-carboxylic acid was suspended in 10 ml of dry dichloromethane. To the resultant suspension was added 0.8 ml of N-methyl-N-(trimethylsilyl)trifluoroacetamide. The mixture was stirred at room temperature for 1 hr to effect silylation. To the silylated solution was added slowly 0.40 ml of iodotrimethylsilane at 0° C. The reaction mixture was allowed to stand at room temperature, stirred for 30 mins, and then concentrated. The concentrate was dissolved in a mixture of 10 ml of acetonitrile and 1.0 ml of tetrahydrofuran to produce a solution. Separately, 202 mg of 2-(1H,3H)-nitromethylen-yl-imidazo[4,5-c]pyridine was dissolved in a mixture of 10 ml of acetonitrile and 0.81 ml of N,O-bis(trimethylsilyl)acetamide. The resulting solution was subjected to silylation for 1.5 hrs to give a silylated pyridine derivative, which was then added to the solution previously obtained. The mixture was allowed to react at room temperature for 3 hrs. Then, to the reaction mixture was added a mixed solvent of 0.5 ml of methyl alcohol and 5 ml of acetonitrile to effect deprotection. The reaction mixture was stirred at 0° C. for 30 mins. Then, the resulting solids were filtered out and dissolved in 10 ml of water while adjusting the pH to 6.5 with sodium bicarbonate, and then concentrated. The residue was purified by column chromatography on silica gel with acetonitrile:water (4:1) to give 165 mg of the title compound.

IR (KBr, cm$^{-1}$): 3400; 2200; 1750; 1652; 1604. NMR (DMSO-d$_6$): 3.14(1H, d); 3.49(1H, d); 3.78(3H, s); 5.14(1H, d); 5.19(1H, d), 5.70(1H, d), 5.80(1H, m); 7.64(1H, d), 8.0(2H, br); 8.75(1H, d); 9.21(1H, s).

EXAMPLE 3

7-β-[(Z)-2-(2-Aminothiazol-4-yl)-2-methoxyiminoacetamido]-3-[2-(1H,3H)-cyanoimine-imidazo[4,5-c]pyridiniummethyl]-3-cephem-4-carboxylate The title compound was prepared by reacting 700 mg of 7-β-[(Z)-2-(2-aminothiazol-4-yl)-2-methoxyiminoacetamido]-3-acetoxymethyl-3-cephem-4-carboxylic acid with 230 mg of 2-(1H,3H)-cyanoimine-imidazo[4,5-c]pyridine by the same procedure as described in Example 1.

Yield: 400 mg. IR (KBr, cm$^{-1}$): 3401; 2180; 1749; 1652. NMR (DMSO-d$_6$): 3.11(1H, d); 3.53(1H, d); 3.81(3H, s); 5.18(1H, d); 5.24(1H, d); 5.77(1H, d); 5.85(1H, m); 6.72(1H, s); 7.20(2H, br); 7.44(1H, d); 8.34(1H,d); 8.57(1H, s); 9.57(1H, d).

EXAMPLE 4

7-β-[(Z)-2-(5-Amino-1,2,4-thiadiazol-3-yl)-2-methoxyiminoacetamido]-3-[2-(1H,3H)-cyanoimine-imidazo[4,5-c]pyridiniummethyl]-3-cephem-4-carboxylate The title compound was prepared by reacting 500 mg of 7-β-[(Z)-2-(5-amino-1,2,4-thiadiazol-3-yl)-2-methoxyiminoacetamido]-3-acetoxymethyl-3-cephem-4-carboxylic acid with 200 mg of 2-(1H,3H)-cyanoimine-imidazo[4,5-c]pyridine by the same procedure as described in Example 2.

Yield: 300 mg. IR (KBr, cm$^{-1}$): 2412; 1750; 1653. NMR (DMSO-d$_6$): 3.12(1H, d); 3.50(1H, d); 3.90(3H, s); 5.12(1H, d); 5.19(1H, d); 5.68(1H, d); 5.83(1H, m); 7.60(1H, d); 8.30(2H, br); 8.72(1H, d); 9.09(1H, s); 9.59(1H, d).

EXAMPLE 5

7-β-[(Z)-2-(5-Amino-1,2,4-thiadiazol-3-yl)-2-methoxyiminoacetamido]-3-[2-(1H,3H)-oxo-imidazo[4,5-c]pyridiniummethyl]-3-cephem-4-carboxylate The title compound was prepared by reacting 500 mg of 7-β-[(Z)-2-(5-amino-1,2,4-thiadiazol-3-yl)-2-methoxyiminoacetamido]-3-acetoxymethyl-3-cephem-4-carboxylic acid with 160 mg of 2-(1H,3H)-oxo-imidazo[4,5-c]pyridine by the same procedure as described in Example 2.

Yield: 300 mg IR (KBr, cm$^{-1}$): 3400; 1750; 1690. NMR (DMSO-d$_6$): 3.1–3.5(2H, q); 4.0(3H, s); 5.1–5.7(2H, q); 5.8(1H,dd); 7.6(1H, s); 8.2(2H, s); 8.8(1H, d); 9.2(1H, s); 9.6(1H, d).

EXAMPLE 6

7-β-[(Z)-2-(5-Amino-1,2,4-thiadiazol-3-yl)-2-methoxyiminoacetamido]-3-[1-methyl-2-(3H)-oxo-imidazo[4,5-c]pyridiniummethyl]-3-cephem-4-carboxylate The title compound was prepared by reacting 500 mg of 7-β-[(Z)-2-(5-amino-1,2,4-thiadiazol-3-yl)-2-methoxyiminoacetamido]-3-acetoxymethyl-3-cephem-4-carboxylic acid with 160 mg of 1-methyl-2-(3H)-oxo-imidazo[4,5-c]pyridine by the same procedure as described in Example 2.

Yield: 300 mg IR (KBr, cm$^{-1}$): 3401; 1750; 1660. NMR (DMSO-d$_6$): 3.10(1H, d); 3.30(1H, d); 3.51(3H, s); 3.61(3H, s); 4.94(1H, d); 5.13(1H, d); 5.49(1H, d); 5.73(1H, m); 7.27(1H, d); 8.02(1H, s); 8.56(1H, d); 8.70(1H, s); 9.62(1H, d).

EXAMPLE 7

7-β-[(Z)-2-(5-Amino-1,2,4-thiadiazol-3-yl)-2-hydroxyiminoacetamido]-3-[2-(1H, 3H)-oxo-imidazo[4,5-c]pyridiniummethyl]-3-cephem-4-carboxylate The title compound was prepared by reacting 500 mg of 7-β-[(Z)-2-(5-amino-1,2,4-thiadiazol-3-yl)-2-hydroxyiminoacetamido]-3-acetoxymethyl-3-cephem-4-carboxylic acid with 190 mg of 2-(1H,3H)-oxo-imidazo[4,5-c]pyridine by the same procedure as described in Example 2.

Yield: 200 mg IR (KBr, cm$^{-1}$): 3300; 1764; 1651; 1612. NMR (DMSO-d$_6$): 3.15(1H, d); 3.59(1H, d); 5.13(1H, d); 5.18(1H, d); 5.70(1H, d); 5.81(1H, d); 7.62(1H, d); 8.78(1H, d); 9.16(1H, d); 9.60(1H, d).

EXAMPLE 8

7-β-[(Z)-2-(5-Amino-1,2,4-thiadiazol-3-yl)-2-carboxymethoxyiminoacetamido]-3-[2-(1H,3H)-oxo-imidazo[4,5-c]pyridiniummethyl]-3-cephem-4-carboxylate The title compound was prepared by reacting 300 mg of 7-β-[(Z)-2-(5-amino-1,2,4-thiadiazol-3-yl)-2-carboxymethoxyiminoacetamido]-3-acetoxymethyl-3-cephem-4-carboxylic acid with 250 mg of 2-(1H,3H)-oxo-imidazo[4,5-c]pyridine by the same procedure as described in Example 2.

Yield: 150 mg. IR (KBr, cm$^{-1}$): 3200; 1760; 1654; 1615. NMR (DMSO-d$_6$): 3.28(1H, d); 3.37(1H, d); 4.50(2H, s); 5.12(1H, d); 5.71(1H, d); 5.85(1H, d); 7.46(1H, d); 8.37(1H, d); 8.70(1H, s); 9.47(1H, d).

EXAMPLE 9

7-β-[(Z)-2-(5-Amino-1,2,4-thiadiazol-3-yl)-2-fluoromethoxyiminoacetamido]-3-[2-(1H, 3H)-oxo-imidazo[4,5-c]pyridiniummethyl]-3-cephem-4-carboxylate The title compound was prepared by reacting 700 mg of 7-β-[(Z)-2-(5-amino-1,2,4-thiadiazol-3-yl)-2-fluoromethoxyiminoacetamido]-3-cephem-4-carboxylic acid with 300 mg of 2-(1H,3H)-oxo-imidazo[4,5-c]pyridine by the same procedure as described in Example 2.

Yield: 300 mg. IR (KBr, cm$^{-1}$): 1761; 1652; 1613. NMR (DMSO-d$_6$): 3.18(1H, d); 3.57(1H, d); 4.51(1H, s); 5.02(3H, s); 5.32(1H, d); 5.83(1H, d); 7.47(1H, d); 8.36(1H, d); 8.47(1H, s); 8.52(1H, d).

EXPERIMENT 1

In vitro Antibacterial Activity

In order to demonstrate the antibacterial activities of the compounds according to the present invention, minimum inhibitory concentration (MIC, μg/ml) for each compound synthesized in the above examples was determined in accordance with the method described in Chemotherapy, 29(1), p. 96 (1981).

As reference compounds, Cefotaxime (CTX), Ceftazidime (CAZ) and Cefpirome (CPR) were employed. The results are shown in Table 1 below.

TABLE 1

Minimum Inhibitory Concentration of the Present Compounds (MIC, μg/ml)

| Strain | Ex. 1 | Ex. 2 | Ex. 3 | Ex. 4 | Ex. 5 | Ex. 6 |
|---|---|---|---|---|---|---|
| 1. S.pyogenes ATCC 8668 | 0.007 | 0.013 | 0.004 | 0.007 | 0.013 | 0.007 |
| 2. S.pyogenes C4003 | 0.007 | 0.007 | 0.004 | 0.007 | 0.013 | 0.004 |
| 3. S.Faecalis ATCC29212 | >100.000 | >100.000 | >100.000 | >100.000 | >100.000 | >100.000 |
| 4. S.aureus Smith | 0.780 | 3.130 | 1.560 | 3.130 | 1.560 | 3.130 |
| 5. S.aureus ATCC29213 | 1.560 | 1.560 | 3.130 | 3.130 | 1.560 | 3.130 |
| 6. S.aureus C4036 | 1.560 | 3.130 | 3.130 | 3.130 | 1.560 | 3.130 |
| 7. MRSA C2208 | >100.000 | >100.000 | >100.000 | >100.000 | >100.000 | >100.000 |
| 8. S.epidermidis ATCC12228 | 0.780 | 1.560 | 0.780 | 1.560 | 0.780 | 1.560 |
| 9. E.coli C4002 | 0.100 | 0.100 | 0.050 | 0.100 | 0.007 | 0.025 |
| 10. E.coli ATCC10536 | 0.050 | 0.050 | 0.013 | 0.050 | 0.004 | 0.007 |
| 11. E.coli ATCC25922 | 0.100 | 0.100 | 0.050 | 0.100 | 0.013 | 0.025 |
| 12. E.cloacae C4008 | 0.050 | 0.050 | 0.013 | 0.050 | 0.002 | 0.013 |
| 13. E.cloacae C4009 | 0.200 | 0.200 | 0.025 | 0.050 | 0.007 | 0.013 |
| 14. K.oxytoca C4022 | 6.250 | 12.500 | 6.250 | 12.500 | 0.780 | 1.560 |
| 15. K.pneumoniae C1040 | 0.025 | 0.050 | 0.025 | 0.025 | 0.004 | 0.007 |
| 16. K.pneumoniae ATCC10031 | 0.025 | 0.050 | 0.007 | 0.013 | 0.004 | 0.007 |
| 17. P.mirabilis ATCC25933 | 0.100 | 0.100 | 0.025 | 0.025 | 0.025 | 0.025 |
| 18. P.rettgeli ATCC9919 | 0.013 | 0.025 | 0.007 | 0.013 | 0.007 | 0.007 |
| 19. S.typhimurium C4045 | 0.100 | 0.200 | 0.025 | 0.050 | 0.007 | 0.025 |
| 20. S.marcescens C1052 | 0.200 | 0.200 | 0.050 | 0.050 | 0.025 | 0.050 |
| 21. S.marcescens ATCC27117 | 0.100 | 0.200 | 0.025 | 0.050 | 0.007 | 0.025 |
| 22. P.aeruginosa C2027 | 6.250 | 6.250 | 6.250 | 6.250 | 0.780 | 1.560 |
| 23. P.aeruginosa ATCC10145 | 50.000 | 50.000 | 12.500 | 12.500 | 1.560 | 1.560 |
| 24. P.aeruginosa ATCC27853 | 50.000 | >100.000 | 6.250 | 25.000 | 0.780 | 3.130 |
| 25. P.aeruginosa C4070 | >100.000 | >100.000 | 12.5001 | 12.500 | 1.560 | 3.130 |

| Strain | Ex. 7 | Ex. 8 | Ex. 9 | CTX | CPR | CAZ |
|---|---|---|---|---|---|---|
| 1. S.pyogenes ATCC 8668 | 0.100 | 0.100 | 0.007 | 0.004 | 0.007 | 0.100 |
| 2. S.pyogenes C4003 | 0.200 | 0.196 | 0.007 | 0.004 | 0.007 | 0.200 |
| 3. S.Faecalis ATCC29212 | >100.000 | >100.000 | >100.000 | >100.000 | 50.000 | >100.000 |
| 4. S.aureus Smith | 6.250 | 3.130 | 1.560 | 1.560 | 0.390 | 6.250 |
| 5. S.aureus ATCC29213 | 0.780 | 0.780 | 1.560 | 1.560 | 0.780 | 6.250 |
| 6. S.aureus C4036 | 1.560 | 1.560 | 3.130 | 1.560 | 0.390 | 6.250 |
| 7. MRSA C2208 | >100.000 | >100.000 | >100.000 | >100.000 | >100.000 | >100.000 |
| 8. S.epidermidis ATCC12228 | 3.130 | 1.560 | 0.780 | 0.780 | 0.200 | 3.130 |
| 9. E.coli C4002 | 6.250 | 3.130 | 0.004 | 0.050 | 0.050 | 0.100 |
| 10. E.coli ATCC10536 | 0.025 | 0.013 | 0.007 | 0.025 | 0.013 | 0.050 |
| 11. E.coli ATCC25922 | 0.050 | 0.050 | 0.026 | 0.100 | 0.050 | 0.200 |
| 12. E.cloacae C4008 | 0.100 | 0.013 | 0.013 | 0.025 | 0.013 | 0.050 |
| 13. E.cloacae C4009 | 0.100 | 0.013 | 0.013 | 0.100 | 0.013 | 0.050 |
| 14. K.oxytoca C4022 | 1.560 | 0.782 | 1.560 | 0.780 | 1.560 | 0.780 |
| 15. K.pneumoniae C1040 | 1.560 | 0.050 | 0.004 | 0.025 | 0.025 | 0.050 |
| 16. K.pneumoniae ATCC10031 | 0.025 | 0.013 | 0.002 | 0.002 | 0.013 | 0.050 |
| 17. P.mirabilis ATCC25933 | 0.100 | 0.050 | 0.025 | 0.025 | 0.050 | 0.050 |
| 18. P.rettgeli ATCC9919 | 0.500 | 0.025 | 0.004 | 0.004 | 0.013 | 0.025 |
| 19. S.typhimurium C4045 | 0.100 | 0.050 | 0.007 | 0.050 | 0.025 | 0.200 |
| 20. S.marcescens C1052 | 0.200 | 0.200 | 0.004 | 0.200 | 0.050 | 0.200 |
| 21. S.marcescens ATCC27117 | 0.100 | 0.100 | 0.007 | 0.100 | 0.050 | 0.100 |
| 22. P.aeruginosa C2027 | 6.250 | 3.130 | 0.780 | 3.130 | 0.390 | 0.780 |
| 23. P.aeruginosa ATCC10145 | 12.500 | 3.130 | 1.560 | 25.000 | 6.250 | 1.560 |
| 24. P.aeruginosa ATCC27853 | 50.000 | 3.130 | 0.780 | 25.000 | 3.130 | 3.130 |
| 25. P.aeruginosa C4070 | 50.000 | 6.250 | 3.130 | 50.000 | 6.250 | 1.560 |

EXPERIMENT 2

Pharmacokinetics (Plasma Half-Life)

In order to investigate the pharmacokinetics properties of the compounds according to the present invention, the plasma half-life was determined in accordance with the method described in Antimicrobial Agents and Chemotherapy, 26(2), p. 204–207 (1984).

In the experiment, the compound synthesized in Example 5 was selected as the test compound, and CAZ and CPR were used as reference compounds. The results are shown in Table 2 below.

TABLE 2

| Compound | Half-Life (T$_{\frac{1}{2}}$, min)* | Remark |
|---|---|---|
| Ceftazidime (CAZ) | 12.3 | SD Rat |
| Cefpirome (CPR) | 19.5 | " |
| Compound of Example 5 | 24.0 | " |

*The half-life shows a mean value.

As can be seen from the foregoing, the compound of the present invention exhibits a significantly longer duration of action than any of the reference compounds.

What is claimed is:

1. A cephem compound having the formula:

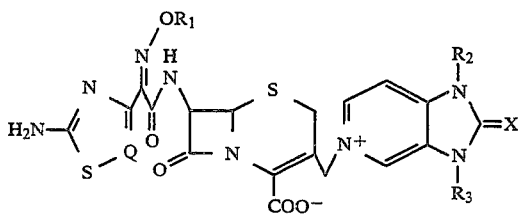

(I)

wherein, Q is a carbon or nitrogen atom; X is an oxygen atom, or a nitroalkyl or cyanoimine group, with the proviso that X cannot be an oxygen atom when Q is a carbon atom; R$_1$ is a hydrogen atom, or a lower alkyl group, or a lower alkyl group which may be substituted by fluoro, or by a carboxylic group or an inorganic cation salt thereof; and R$_2$ and R$_3$ independently are a hydrogen atom or a lower alkyl group; or pharmaceutically acceptable salts thereof.

2. The compound of claim 1, wherein the compound of formula (I) is one of the following compounds:

7-β-[(Z)-2-(2-aminothiazol-4-yl)-2-methoxyiminoacetamido]-3-[2-(1H,3H)-nitromethylen-yl-imidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[2-(1H,3H)-nitromethylen-yl-imidazo[4,5-c]pyridiniummethyl]-3-cephem-4-carboxylate;

7-β-[(Z)-2-(2-aminothiazol-4-yl)-2-methoxyiminoacetamido]-3-[2-(1H,3H)-cyanoimine-imidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[2-(1H,3H)-cyanoimine-imidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[2-(1H,3H)-oxo-imidazo[4,5-c]pyridiniummethyl]-3-cephem-4-carboxylate;

7-β-[(Z)-2-(5-amino-1,2,4-thiadiazol-3-yl)-2-methoxyiminoacetamido]-3-[1-methyl-2-(3H)-oxo-imidazo[4,5-c]pyridiniummethyl]-3-cephem-4-carboxylate;

7-β-[(Z)-2-(5-amino-1,2,4-thiadiazol-3-yl)-2-hydroxyiminoacetamido]-3-[2-(1H,3H)-oxo-imidazo[4,5-c]pyridiniummethyl]-3-cephem-4-carboxylate;

7-β-[(Z)-2-(5-amino-1,2,4-thiadiazol-3-yl)-2-carboxymethoxyiminoacetamido]-3-[2-(1H,3H)-oxo-imidazo[4,5-c]pyridiniummethyl]-3-cephem-4-carboxylate; and 7-β-[(Z)-2-(5-amino-1,2,4-thiadiazol-3-yl)-2-fluoromethoxyiminoacetamido]-3-[2-(1H,3H)-oxo-imidazo[4,5-c]pyridiniummethyl]-3-cephem-4-carboxylate.

3. A pharmaceutical composition containing an antibacterially effective amount of a cephera compound according to claim 1.

4. A pharmaceutical composition containing an antibacterially effective amount of a cephera compound according to claim 2.

5. A method of treating gram-negative bacterial infection in a host comprising administering to a gram-negative bacteria infected host an effective amount of a cephem compound according to claim 1.

6. The method of claim 5 wherein the gram-negative bacteria comprise Pseudomonas.

7. A method of treating gram-negative bacterial infection in a host comprising administering to a gram-negative bacteria infected host an effective amount of a cephem compound according to claim 2.

8. The method of claim 7 wherein the gram-negative bacteria comprise Pseudomonas.

* * * * *